United States Patent [19]

White et al.

[11] Patent Number: 4,474,782

[45] Date of Patent: Oct. 2, 1984

[54] ALKENYL AND ALKYNYL MORPHOLINE COMPOUNDS, COMPOSITIONS AND USE

[75] Inventors: Alan C. White, Windsor; Edwin T. Edington, Cookham, both of England

[73] Assignee: John Wyeth & Brother, Ltd., Maidenhead, England

[21] Appl. No.: 582,995

[22] Filed: Feb. 24, 1984

[30] Foreign Application Priority Data

Mar. 1, 1983 [GB] United Kingdom ............... 8305638

[51] Int. Cl.³ ............... A61K 31/535; C07D 265/30
[52] U.S. Cl. ............... 424/248.58; 544/152; 544/173; 544/174
[58] Field of Search ............... 544/152, 173, 174; 424/248.58

[56] References Cited

U.S. PATENT DOCUMENTS 3,154,544 10/1964 Langdon et al. ............... 544/174
4,360,519 11/1982 White et al. ............... 544/173

Primary Examiner—Robert W. Ramsuer

Attorney, Agent, or Firm—Arthur G. Seifert

[57] ABSTRACT

Morpholine derivatives of the formula

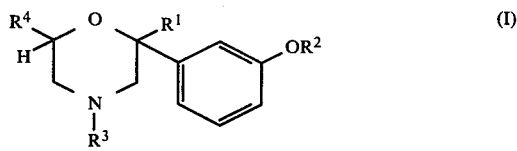

and their pharmaceutically acceptable acid addition salts possess analgesic and/or opiate antagonistic activity. In the formula $R^1$ represents lower alkyl; $R^2$ represents hydrogen, lower alkyl or (lower)alkoxymethyl; $R^3$ represents hydrogen, lower alkyl, lower alkenyl, lower alkynyl, aryl(lower)alkyl, 2-tetrahydrofurylmethyl or cycloalkylmethyl and $R^4$ represents a lower alkenyl or lower alkynyl group containing at least 3 carbon atoms and in which there is no unsaturated bond in the 1-position.

5 Claims, No Drawings

ALKENYL AND ALKYNYL MORPHOLINE COMPOUNDS, COMPOSITIONS AND USE

This invention relates to morpholine derivatives, to processes for their preparation and to pharmaceutical compositions containing them.

The present invention provides novel morpholine derivatives of the general formula (I)

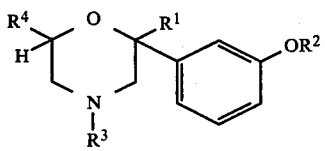

and their pharmaceutically acceptable acid addition salts. In the formula $R^1$ represents lower alkyl; $R^2$ represents hydrogen, lower alkyl or (lower)alkoxymethyl; $R^3$ represents hydrogen, lower alkyl, lower alkenyl, lower alkynyl, aryl (lower)alkyl, 2-tetrahydrofurylmethyl or cycloalkylmethyl and $R^4$ represents a lower alkenyl or lower alkynyl group containing at least 3 carbon atoms and in which there is no unsaturated bond in the 1-position.

The term "lower" as used herein means that the radical referred to contains 1 to 6 carbon atoms. The radical preferably contains 1 to 4 carbon atoms. For example when any of the groups $R^1$, $R^2$ and $R^3$ is a lower alkyl group the radical may be, for example, methyl, ethyl, propyl or butyl. Suitable groups for $R^4$ and also for $R^3$, when it is lower alkenyl or lower alkynyl, include, for examle, allyl, 2-methyl-2-propenyl, 3-methylbut-2-enyl and propynyl. When $R^3$ is cycloalkylmethyl the group is preferably cyclopropylmethyl or cyclobutylmethyl. When $R^3$ is aryl (lower) alkyl the group can be, for example, benzyl or phenethyl. When $R^2$ is an acyl group it is preferably a lower alkanoyl group such as acetyl, propionyl or butyryl. When $R^2$ is a (lower)alkoxymethyl group it is preferably a methoxymethyl group.

Preferably, $R^1$ is an ethyl group, $R^2$ is hydrogen, $R^3$ is lower alkyl (e.g. methyl) and $R^4$ is lower alkenyl (e.g. allyl).

The compounds of the invention may be prepared by reduction of a compound of general formula (II)

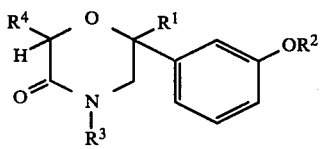

wherein $R^1$, $R^2$, $R^3$ and $R^4$ are as defined above, and if desired converting a free base of general formula (I) into a pharmaceutically acceptable acid addition salt thereof. The compound of general formula (II) can be reduced with, for example, a hydride transfer agent (e.g. lithium aluminium hydride).

Once a compound of general formula (I) has been prepared it may be converted into another compound of general formula (I) by methods known per se. For example, a compound in which $R^3$ is lower alkyl, lower alkenyl, lower alkynyl, aryl(lower)alkyl, 2-tetrahydrofurylmethyl or cycloalkylmethyl may be prepared by "N-alkylating" a compound in which $R^3$ is hydrogen. By "N-alkylating" is meant introducing on to the nitrogen atom of the morpholine ring a lower alkyl, lower alkenyl, lower alkynyl, aryl(lower)alkyl, 2-tetrahydrofurylmethyl or cycloalkylmethyl radical. In one method of carrying out the "N-alkylating" process a compound of general formula I in which $R^3$ is hydrogen is reacted with a halide of general formula

$R^{3'}$—Hal where $R^{3'}$ is lower alkyl, lower alkenyl, lower alkynyl, aryl(lower)alkyl, 2-tetrahydrofurylmethyl or cycloalkylmethyl in the presence of an acid acceptor such as an alkali metal carbonate (e.g. potassium carbonate), preferably in solution in an organic solvent.

Alternatively the compound of general formula (I) in which $R^3$ is hydrogen may be alkylated by reductive alkylation e.g. by treatment with an aldehyde and sodium cyanoborohydride. A preferred method of cycloalkylmethylating involves reacting the N-unsubstituted compound with a cycloalkylcarbonyl chloride to give an intermediate N-carbonyl cycloalkyl compound which may be reduced with, for example, a hydride transfer agent.

A compound of general formula (I) in which $R^2$ is a hydrogen atom can be obtained from a corresponding compound in which $R^2$ is lower alkyl or lower alkoxymethyl by splitting off the ether group in known manner, e.g. by treating the lower alkyl ether with an alkali metal propane thiolate or by treating the (lower)alkoxymethyl ether with dilute acid. Compounds in which $R^3$ is lower alkyl, particularly methyl may be dealkylated to compounds in which $R^3$ is hydrogen, e.g. by reaction with ethyl-, phenyl-, vinyl- or 2,2,2,-trichloroethylchloroformate followed by removal of the resulting N-substituent with, for example, dilute acid or zinc and acetic acid or basic conditions as appropriate.

A compound of general formula (I) in which $R^2$ is hydrogen can be acylated (e.g. with acetic anhydride) to give a corresponding compound in which $R^2$ is an acyl group such as a lower alkanoyl radical.

Two or more of the above mentioned processes for interconverting the compounds of general formula (I) may, if desired, be carried out consecutively. In some instances it may be necessary to protect one or more of the functional groups on the molecule while reaction occurs at another functional group and then subsequently remove the protecting group or groups.

The compounds of general formula (II) may be prepared by (lower)alkenylating or (lower)alkynylating (wherein the lower alkenyl or lower alkynyl group is a group of formula $R^4$ as defined above) a compound of general formula (III)

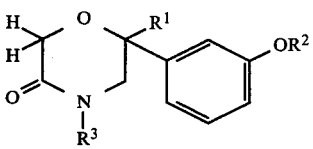

Wherein $R^1$, $R^2$ and $R^3$ have the meanings given above. The alkenylation or alkynylation may be effected with a (lower)alkenylating or (lower)alkynylating agent in the presence of an amide base. The agent may be, for example, a lower alkenyl or alkynyl halide, sulphate or tosylate. Examples of amide bases are lithium diisopropylamide, lithium tetramethylpiperidine and N-tertiarybutylcyclohexylamide or other compounds of formula MA where M is sodium, potassium or lithium and A is a secondary amine radical. The amide base may be formed in situ by reaction of a metal compound MR (where M is sodium, potassium or lithium and R is alkyl, aryl or aralkyl) with a secondary amine.

The compounds of general formula (III) may be prepared by the processes described, for example, in UK patent application No. 2089796A.

If in any of the processes described above the compound of the invention is obtained as an acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methane-sulphonic and p-toluenesulphonic acids.

The compounds of the invention possess two asymmetric carbon atoms and the compounds may exist in various stereochemical forms. Mixtures of diastereoisomers may be separated, for example, by chromatography (e.g. high performance liquid chromatography) of fractional crystallisation. The ratio of the diastereoisomers in the mixture may be affected by the choice of reagent used in the process to produce the starting materials or final compounds. Optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired compound provided further chemical reaction does not cause racemisation.

The novel compounds of the invention possess pharmacological activity, in particular analgesic activity and/or opiate antagonistic activity as indicated by standard pharmacological testing. For example, 3-[2R*,6S*)-2-ethyl-4-methyl-6-(2-propenyl)-2-morpholinyl]phenol, a representative compound of the invention, exhibits opiate antagonistic activity when tested by a procedure based upon Aceto et al, Brit. J. Pharmac., 1969, 36, 225-239. The compound had a $ED_{50}$ of 0.18 mg/kg s.c. Confirmation of the potent opiate antagonistic activity of the above mentioned compound is shown by the effect on the binding of radiolabelled naloxone in mouse brain homogenates in the presence and absence of sodium ions. The results revealed an $IC_{50}$ in displacing tritiated naloxone in the absence of sodium of 62 nM and 25 nM in the presence of sodium giving a sodium ratio of 0.4. This low sodium response ratio confirms the opiate antagonistic activity of the compound.

The analgesic activity of the compounds of the invention can be determined in, for example, a phenylbenzoquinone-induced writhing test (based upon E. Siegmund et al., Proc. Soc. Exp. Biol. Med., 1957, 95, 729-731). Some of the compounds of the invention are useful as intermediates for other compounds of the invention by the methods described above.

The invention provides a pharmaceutical composition comprising a compound of general formula (I) or a pharmaceutically acceptable salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, lactose, pectin, dextrin, starch, gelatin, tragacanth, methylcellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The following Examples illustrate the invention:

EXAMPLE 1

6-Ethyl-6-(3-methoxyphenyl)-4-methyl-1-(2-propenyl)-3-morpholinone

6-Ethyl-6-(3-methoxyphenyl)-4-methyl-3-morpholinone (30.9 mM 7.7 g) in dry THF (50 mL) was added to a solution of lithium diisopropylamide (from 1.55 M butyl lithium in hexane, 22 mL, and diisopropylamine, 3.34 g, 4.6 ml in tetrahydrofuran, 50 mL). After stirring for 30 minutes at 0° 3-bromopropene (3.99 g, 2.7 mL) in THF (50 mL) was added rapidly. The mixture was stirred for 2 hours at room temperature and then added to ice and hydrochloric acid and the product extracted with toluene and ether. The product was dried (MgSO$_4$) and filtered and the resulting crude title compound was used in Example 2.

EXAMPLE 2

6-Ethyl-6-(3-methoxyphenyl)-4-methyl-2-(2-propenyl)-morpholine

The crude product from Example 1 (8 g) in dry ether (50 mL) was added to a suspension of lithium aluminium hydride (3.5 g) in ether (100 mL). After stirring overnight the mixture was treated with water (3 mL), 4N sodium hydroxide (7 mL) and water (3 mL). The mixture was filtered, washed with hot toluene and extracted with acid/base to yield the title compound as an oil (4.2 g) containing a mixture of diastereoisomers. The isomers were separated by chromatography on silica and the obtained (2R*,6S*)-isomer was used in Example 3.

EXAMPLE 3

3-[(2R*,6S*)-2-Ethyl-4-methyl-6-(2-propenyl)-2-morpholinyl]phenol (2R*,6S*)-6-ethyl-6-(3-methoxyphenyl)-4-methyl-2-(2-propenyl) morphine (900 mg) in dry DMF (20 mL) was added to a stirred solution of sodium propylthiolate (from sodium hydride 50% dispersion in oil, 0.192 g, 6 mM and propanethiol, 16 mM, 1.22 g, 1.45 mL) in DMF (10 mL). The reaction mixture was stirred and heated under reflux until TLC indicated that the reaction was complete. After standing overnight, the solvent was removed, under reduced pressure, made alkaline with 2M sodium hydroxide and extracted with ether which was discarded. The aqueous layer was then saturated with ammonium chloride and extracted into ether. These ether extracts were dried (MgSO$_4$) and the solvent removed under reduced pressure. The residue was converted to the tosylate salt in isopropyl alcohol/ether and recrystallised from isopropyl alcohol to give the title compound as the tosylate (476 mg), m.p. 193°-4°.

Analysis: Found: C, 63.4; H, 7.2; N, 3.2%. $C_{16}H_{23}NO_2 \cdot C_7H_7SO_3H$ requires: C, 63.7; H, 7.2; N, 3.2%.

NMR data support the 2R*,6S*-configuration of the product.

EXAMPLE 4

(a)
6-Ethyl-6-(3-methoxyphenyl)-4-methyl-6-(2-propynyl)-3-morpholinone

6-Ethyl-6-(3-methoxyphenol)-4-methyl-3-morpholinone (0.01 mole) in dry tetrahydrofuran (20 mL) is added dropwise to a stirred solution of lithium diisopropylamide (0.022 mole) in THF/hexane (60 mL) under nitrogen. After stirring at room temperature for 15 minutes, 3-bromopropynyl (0.1 mole) in THF (30 mL) is added dropwise. The reaction is stirred at room temperature for 1 hour then poured onto a mixture of ice and dilute hydrochloric acid. The aqueous layer is separated, and extracted with dichloromethane (3×20 mL). The combined organic extracts are washed with water, dried (MgSO$_4$) and evaporated to give the title compound which is used crude in the reduction stage.

(b) (2R*,6R*) and (2R*,6S*)3-ethyl-3-(3-methoxyphenyl)-4-methyl-6-(2-propynyl)-morpholine Crude 6-ethyl-6-(3-methoxyphenyl)-4-methyl-6-(2-propynyl) 3-morpholinone from the above example 4(a), in ether (50 mL) is added dropwise to a stirred suspension of lithium aluminium hydride (2 g) in ether (150 mL). The reaction is heated and stirred under reflux for 2 hours. After cooling, the reaction mixture is decomposed by the addition of water (2 mL), 4M sodium hydroxide solution (2 mL) and water (4 mL). The precipitate is filtered and washed with ether (4×100 mL). After drying (MgSO$_4$) the solvent is removed and the product is separated into its (2R*,6R*) and (2R*,6S*) diastereoisomers by chromatography on silica using ethylacetate triethylamine (1–3%) as eluant.

(c) (2R*,6S*) (6-ethyl-4-methyl-6-(2-propynyl)-3-morpholinyl) phenol

The (2R*,6S*) diastereoisomer from the above experiment is heated with stirring at 140° C. under N$_2$, in dimethyl formamide (50 mL) containing three equivalents of sodium propylmercaptide for 6 hours. When the reaction is complete, the dimethylformamide is removed under reduced pressure. The product is poured into water and after acidification extracted with ether (3×25 mL). The aqueous layer is basified with concentrated aqueous ammonia and extracted with dichloromethane (3×20 mL). After drying the solvent is removed under reduced pressure to leave the title compound which is converted to a suitable crystalline salt.

We claim:

1. A compound selected from the group consisting of a morpholine derivative of the general formula

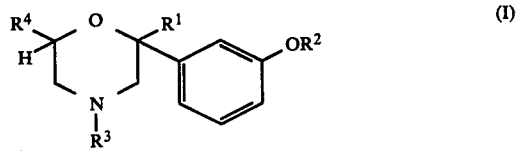

and a pharmaceutically acceptable acid addition salt thereof, wherein R$^1$ represents lower alkyl; R$^2$ represents hydrogen, lower alkyl or (lower)alkoxymethyl; R$^3$ represents hydrogen, lower alkyl, lower alkenyl, lower alkynyl, aryl(lower)alkyl, 2-tetrahydrofurylmethyl or cycloalkylmethyl and R$^4$ represents a lower alkenyl or lower alkynyl group containing at least 3 carbon atoms and in which there is no unsaturated bond in the 1-position.

2. A compound as claimed in claim 1 wherein R$^3$ is lower alkyl, R$^4$ is lower alkenyl and R$^2$ is hydrogen.

3. A compound according to claim 1 which is 3-[2-ethyl-4-methyl-6-(2-propenyl)-2-morpholinyl]phenol.

4. A pharmaceutical composition having analgesic or opiate antagonistic activity comprising a compound selected from the group consisting of a morpholine derivative of the general formula

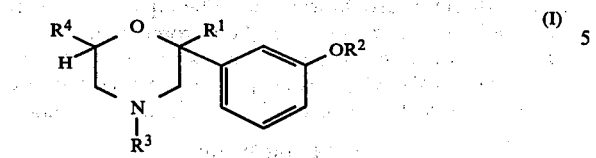

and a pharmaceutically acceptable acid addition salt thereof, wherein $R^1$ represents lower alkyl; $R^2$ represents hydrogen, lower alkyl or (lower)alkoxymethyl; $R^3$ represents hydrogen, lower alkyl, lower alkenyl, lower alkynyl, aryl(lower)alkyl, 2-tetrahydrofurylmethyl or cycloalkylmethyl and $R^4$ represents a lower alkenyl or lower alkynyl group containing at least 3 carbon atoms and in which there is no unsaturated bond in the 1-position in association with a pharmaceutically acceptable carrier.

5. A method of treating a mammal in need of an analgesic or opiate antagonist which comprises administering to said animal an analgesically or opiate antagonistically effective amount of a compound selected from the group consisting of a morpholine derivative of the general formula

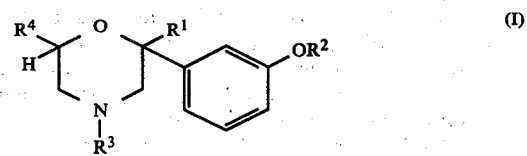

and a pharmaceutically acceptable acid addition salt thereof, wherein $R^1$ represents lower alkyl; $R^2$ represents hydrogen, lower alkyl or (lower)alkoxymethyl; $R^3$ represents hydrogen, lower alkyl, lower alkenyl, lower alkynyl, aryl(lower)alkyl, 2-tetrahydrofurylmethyl or cycloalkylmethyl and $R^4$ represents a lower alkenyl or lower alkynyl group containing at least 3 carbon atoms and in which there is no unsaturated bond in the 1-position.

* * * * *